(12) United States Patent
Crofford et al.

(10) Patent No.: US 8,801,799 B2
(45) Date of Patent: Aug. 12, 2014

(54) FEMORAL HEAD PROSTHESIS

(75) Inventors: Theodore Crofford, Forth Worth, TX (US); Michael Santarella, Essex Fells, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1182 days.

(21) Appl. No.: 12/220,433

(22) Filed: Jul. 24, 2008

(65) Prior Publication Data

US 2010/0023131 A1    Jan. 28, 2010

(51) Int. Cl.
A61F 2/36    (2006.01)

(52) U.S. Cl.
USPC .................................... 623/23.14; 623/23.12

(58) Field of Classification Search
USPC ............ 623/20.34, 20.36, 22.4, 22.44, 22.46, 623/23.11–23.38, 23.44
See application file for complete search history.

(56) References Cited

U.S. PATENT DOCUMENTS

| | | |
|---|---|---|
| 4,005,495 A | 2/1977 | Locke et al. |
| 4,129,903 A | 12/1978 | Huggler et al. |
| 4,224,699 A | 9/1980 | Weber et al. |
| 4,795,473 A | 1/1989 | Grimes |
| 4,976,740 A | 12/1990 | Kleiner |
| 4,986,834 A * | 1/1991 | Smith et al. ................ 623/23.32 |
| 4,998,937 A | 3/1991 | Grimes |
| 5,035,717 A | 7/1991 | Brooks et al. |
| 5,133,760 A | 7/1992 | Petersen et al. |
| 5,147,403 A | 9/1992 | Gitelis |
| 5,318,571 A | 6/1994 | Benson |
| 5,320,625 A | 6/1994 | Bertin |
| 5,342,363 A | 8/1994 | Richelsoph |
| 5,376,125 A | 12/1994 | Winkler et al. |
| 5,571,203 A | 11/1996 | Masini |

(Continued)

FOREIGN PATENT DOCUMENTS

| | | |
|---|---|---|
| DE | 19725269 | 1/1999 |
| DE | 19834277 | 2/2000 |

(Continued)

OTHER PUBLICATIONS

Harlan C. Amstutz, MD and Peter Grigoris, MD, PhD; Metal on Metal Bearings in Hip Arthroplasty; Clinical Orthopaedics and Related Research, 1996, No. 329S; pp. S11-S34.

(Continued)

*Primary Examiner* — Thomas J Sweet
*Assistant Examiner* — Megan Wolf
(74) *Attorney, Agent, or Firm* — Lerner, David, Littenberg, Krumholz & Mentlik, LLP (57) ABSTRACT

An implant is provided for replacing the proximal portion of a femur having a substantially intact natural femoral neck and a lateral side opposite the femoral neck, with a bore extending from the femoral neck through a lateral side of the femur. The implant comprises a sleeve having a flange for engaging a proximally facing resected surface of the neck surrounding the bore in the femur and having a bore with an inwardly tapered conical portion. A shaft member having a longitudinal axis, a distal end, and a proximal end is placed in the bore through the femur. The shaft member has an intermediate conically tapered male portion for coupling to the conically tapered bore of the sleeve and a proximal end having a conically tapered portion. A head member having a distal end and a proximal substantially-spherical portion and a tapered recess is configured for positioning in a natural or prosthetic hip socket.

12 Claims, 6 Drawing Sheets

(56) References Cited

U.S. PATENT DOCUMENTS

| | | | |
|---|---|---|---|
| 5,741,262 | A | 4/1998 | Albrektsson et al. |
| 5,766,263 | A | 6/1998 | Grundei et al. |
| 5,800,553 | A | 9/1998 | Albrektsson et al. |
| 5,976,148 | A | 11/1999 | Charpenet et al. |
| 5,980,575 | A | 11/1999 | Albrektsson et al. |
| 6,120,510 | A | 9/2000 | Albrektsson et al. |
| 6,231,611 | B1 | 5/2001 | Mosseri et al. |
| 6,273,915 | B1 | 8/2001 | Grimes |
| 6,284,002 | B1 | 9/2001 | Sotereanos |
| 6,379,390 | B1 | 4/2002 | Advani et al. |
| 6,383,227 | B1 | 5/2002 | Baroud et al. |
| 6,482,237 | B2 | 11/2002 | Mosseri |
| 6,508,841 | B2 | 1/2003 | Martin et al. |
| 6,616,697 | B2 | 9/2003 | Sotereanos |
| 6,626,948 | B2 * | 9/2003 | Storer et al. ............ 623/23.14 |
| 6,695,883 | B2 | 2/2004 | Crofford |
| 6,706,073 | B2 | 3/2004 | Draenert et al. |
| 6,723,102 | B2 | 4/2004 | Johnson et al. |
| 6,770,100 | B2 | 8/2004 | Draenert |
| 7,104,995 | B2 | 9/2006 | Crofford |
| 7,156,879 | B1 * | 1/2007 | Albrektsson et al. ...... 623/23.14 |
| 2002/0059000 | A1 | 5/2002 | Dwyer et al. |
| 2002/0095217 | A1 | 7/2002 | Masini |
| 2002/0143402 | A1 | 10/2002 | Steinberg |
| 2004/0193278 | A1 * | 9/2004 | Maroney et al. .......... 623/19.14 |
| 2005/0049712 | A1 | 3/2005 | Ondrla et al. |

FOREIGN PATENT DOCUMENTS

| | | |
|---|---|---|
| EP | 0099167 | 1/1984 |
| EP | 0791342 | 8/1997 |
| EP | 1120096 A1 | 8/2001 |
| FR | 1075914 | 10/1954 |
| GB | 2033755 | 5/1980 |
| WO | 8603962 | 7/1986 |
| WO | 8911837 | 12/1989 |
| WO | 9316663 | 9/1993 |
| WO | 9725939 | 7/1997 |

OTHER PUBLICATIONS

A.H. Huggler, and H.A.C. Jacob (Eds.); The Thrust Plate Hip Prosthesis; Springer-Verlag Berlin Heidelberg 1997; 3 pages submitted.

Tomas Albrektsson, MD, PhD, Lars V. Carlsson, MD, PhD, Magnus Jacobsson, MD, PhD, and Warren MacDonald, CEng, MPhil; Clinical Orthopaedics and Related Research, 1998, No. 352; pp. 81-94.

Prof. Dr. A.H. Huggler and Dr. Ing. H.A.C. Jacob; The Thrust Plate Process; All Pro; Jan. 1993, 16 pages.

A.H. Huggler and H.A.C. Jacob; The Uncemented Thrust-Pate Hip Prosthesis; Date Unknown; pp. 125-129.

H. Bereiter, A.H. Huggler. H.A.C. Jacob, and P. Seemann; The Thrust Plate Prosthesis (TPP) A New Concept in Hip Prosthesis Design Eight Years of Clinical Experience; Orthop Rel. Sci. 2, Date Unknown; pp. 191-202.

International Search Report, PCT/US09/04333, dated Mar. 2, 2010.

\* cited by examiner

FEMORAL HEAD PROSTHESIS

BACKGROUND OF THE INVENTION

The present application relates to an improved apparatus and method for hip replacements, and more specifically to a less-invasive prosthetic which replaces the femoral head while retaining the natural femoral neck.

A widely used design for replacement of the proximal portion of a femur employs an elongate, often curved, shaft that extends into the medullary canal of the femur. This design may place unnatural stresses on the femur which lead to pain and the consequential curtailment of activity for the patient. Further, present techniques can lead to proximal bone loss and call for the resection of the majority of the femoral neck. Current designs also call for fixing the prosthesis in the proximal third of the femur. The useful life of an intramedullary implant is often less than the expected life span of a young patient.

Previously known prostheses for replacing a femoral head that do not extend into the medullary canal have been mechanically complex or have proven troublesome in actual use. Huggler, U.S. Pat. No. 4,129,902 and Grimes, U.S. Pat. No. 4,795,473 are examples of prosthetic implants having a side plate attached to the exterior lateral side of the femur opposite the femoral head. Screws are used to secure the plate to the femur and one or more holes are drilled into the femur for securing the plate to the bone. The additional holes and the stresses at the site of fixation are believed to cause trauma to the bone.

Masini, U.S. Pat. No. 5,571,203 discloses a device having a shaft that extends through a resected portion of the proximal femur, positioned co-axially relative to the longitudinal axis of the femur. The device is secured by a screw or similar locking device that extends into the femur from the lateral side, just below the greater trochanter.

A conventional method for implanting the above types of femoral head implants is described in Campbell's Operative Orthopaedics, (Mosby, $7^{th}$ ed., 1987) and typically includes making a large incision in the patient's lateral side at the hip joint and through the skin and muscle, dislocating the hip and then sawing off the femoral head. This method is considered invasive because of the need to dislocate the hip and cut through muscle surrounding the hip joint. Invasive procedures increase the trauma to the patient, the potential for complications, recovery time and the cost.

Replacement of the proximal portion of the femur is sometimes necessary due to degenerative bone disorders or trauma to otherwise healthy bone caused by accidental injury. In the latter instance it is desirable to replace the traumatized portion of the bone without causing further trauma to healthy bone. There is a need, therefore, for an implant that replaces a traumatized portion of the femur, but also significantly minimizes stress to the remaining healthy bone and that can be implanted by a method that is less invasive.

There are several other significant remaining problems and issues relating to hip arthroplasty. They include:

The Young, Active Patient:

Younger patients are more likely to have failure of their primary arthroplasty both due to increased demand on the mechanical construct, and from a pure life expectancy standpoint. It follows that they are more likely to require a revision and a second revision, which may lead to a catastrophic bone loss situation.

Instability:

This problem still occurs at the same rate that it did 50 years ago. Larger femoral heads may decrease the incidence, but no other significant technical changes have occurred to effect the incidence of this serious complication.

Bone Loss:

The overwhelming majority of present successful femoral prosthesis achieves fixation at least as far distal as the proximal femoral metaphysic. When these prostheses fail, the next step usually involves diaphyseal fixation, often with a large diameter stiff stem.

Leg Length Inequality:

Leg length inequality after hip arthroplasty has always been a problem and an average lengthening of the leg of 1 centimeter is common. Lengthening is sometimes accepted for the sake of improved stability. Leg length inequality has been reported as the number one reason why surgeons are sued after hip arthroplasty.

Surgical Morbidity:

Hip arthroplasty usually involves significant blood loss, body fluid alterations and pain. If the operation can be made smaller, with less blood loss and less pain without diminishing long term results, every effort should be made to do so.

It would therefore be desirable to provide a femoral next prosthetic apparatus that overcomes these significant disadvantages.

A modular femoral neck fixation prosthesis that addresses these problems is described in U.S. Pat. No. 6,695,883 listing Dr. Theodore Crofford as inventor. U.S. Pat. No. 6,695,883, the disclosure of which is incorporated herein by reference, teaches that the resection level should not be at the isthmus of the neck, but at the transition of the femoral head to neck region. This region is much larger in diameter than any geometry at the vicinity of the neck isthmus. It is believed that this location does not provide an optimum load transfer from the implant to the bone. Also the large size of the implant disclosed tends to transfer anatomic loads away from the neck region and into the metaphysic region of the femur. In addition to the large rigid construct of the neck prosthesis, a secondary rigid member is attached to the prosthesis body to increase its total length to span the distance between the neck resection and lateral cortex. This has the effect of creating a high stiffness construct in the metaphysic region of the femur thereby transferring a disproportionate amount of anatomical load away from host anatomy.

SUMMARY OF THE INVENTION

The present invention addresses these issues with the basic design theory of reducing the stiffness of the implant construct to better match that of the host bone and localize the direct bearing loads in the proximal neck. This is accomplished utilizing a modular construct comprised of a femoral bearing, a neck sleeve, and a shaft of intermediate member. The components utilize taper junctions to mate both the femoral bearing to the intermediate member and the neck sleeve to the intermediate member.

The sleeve is comprised of a body of revolution having a large diameter flange at the proximal end and a cylindrical body of relatively short diameter to length ratio at the distal end. Along the longitudinal axis is tapered mating junction. All surfaces in contact with the host bone other than the portion under the sleeve collar and sliding distal tip have a substrate that is designed for boney in-growth or on-growth. The proximal flange of the implant is of sufficient diameter to completely cover the resected neck surface and create a seal between the implant flange and resected segment. The short diameter to length ratio of the neck sleeve coupled with the large diameter flange localizes the physiological forces to the region of the proximal neck and away from the metaphysic. A multitude of flange and body diameters as well as cross-sectional shapes are available to match the patient anatomy are proposed. The interlocking tapers on all the various size components are preferably of the same size.

The offset loading scenario created by anatomical loads acting through an offset femoral bearing induces a force-couple loading scenario. The sleeve distributes the compressive forces to the neck region as previously described, and the intermediate member counters the physiologically induced bending couple by bearing against or through the lateral cortex. This countering force-couple action stabilizes the construct within the femoral neck region of the femur. The construction of the intermediate member is a body of revolution consisting of a tapered proximal end to mate with a femoral bearing, a tapered mid-section to mate with the sleeve and a contoured distal bending section.

As stated above, the design objective is to reduce the stiffness of the implant construct to better match that of the host bone thereby increasing the amount of load sharing between the implant and host bone. In order to accomplish this, the distal section of the preferred intermediate member has three distinct features working collectively to provide longevity, stability, and flexibility. Ordered distally from the tapered mating junction, the first distinct feature is a controlled transition region from the relatively large diameter of the tapered junction to the smaller diameter middle section. As it is a transition region, its purpose is to minimize any stress concentrations caused by bending in that vicinity. In this example, an optimized elliptical fillet is utilized as the transition geometry. The second feature located at the middle section is a reduced stiffness region that is able to transmit the functional loads while being made flexible by reducing its bending section. The middle section is optimized to maintain sufficient strength for longevity while being made flexible to match the stiffness of the proximal femur. Lastly, the distal end of the intermediate member comprises a transition region and a bearing section that interacts directly with the lateral wall of the femur. Again there is a contoured transition region to the increased diameter of the bearing section area, and the bearing area is optimized to reduce the bearing stress at the implant/bone interface.

Aspects of the invention are provided by a method for resurfacing the head of a femur which includes resecting a neck of the femur at or proximally of the narrowest cross-section thereof. A bore is formed in the femur through the resected neck, through the proximal femur and through the lateral cortex of the femur. A sleeve having a flange for engaging a proximally facing resected surface of the neck and having a bore with an inwardly tapered conical portion is inserted in the neck with the bore therein aligned with the bore in the femur. A one-piece shaft element having an intermediate conically tapered male portion for mating with the tapered portion of the sleeve bore is inserted into the sleeve. The shaft element has a proximal end including a conically tapered proximal end portion and a distal shaft portion extending on respective sides of the intermediate portion. The distal shaft portion extends beyond the surface of the lateral cortex of the femur and has an unthreaded tip portion with a diameter less than or equal to a diameter of the bore in the femur. A part-spherical prosthetic head is mounted on the proximal tapered male surface of the shaft element.

The distal shaft portion of the shaft element may have an inwardly tapered section and a distal tip having a diameter generally equal to the diameter of the bore in the femur.

The distal stem of the shaft element may have a first portion which tapers inwardly from a proximal end towards the distal tip.

The shaft element may have a groove with a diameter less than a minimum diameter of both the intermediate tapered portion and the proximal tapered end portion.

The distal shaft end of the shaft may include a second portion distal of the first portion which tapers outwardly towards the distal tip.

Other aspects of the invention are provided by an implant for replacing the proximal portion of a femur having a substantially intact natural femoral neck and a lateral side opposite the femoral neck, with a bore extending from the femoral neck through a lateral side of the femur. The implant comprises a sleeve having a flange for engaging a proximally facing resected surface of the neck surrounding the bore in the femur. The sleeve has a bore with an inwardly tapered conical portion. The implant includes a solid body member having a longitudinal axis, a distal end, and a proximal end. The solid body being configured for positioning, in use, in the bore through the femur. The solid body member has an intermediate conically tapered male portion for coupling to the conically tapered bore of the sleeve and a proximal end having a conically tapered portion. The implant further includes a head member having a distal end and a proximal substantially-spherical portion configured for positioning in a natural or prosthetic hip socket, the distal end including a conically tapered bore for coupling to the proximal conically tapered portion of the solid body member, when implanted. No threaded elements pass within or through the femur.

The solid body has a distal shaft portion having an inwardly tapered section. The distal shaft has a distal tip having a diameter generally equal to or less than the diameter of the bore in the femur.

The distal shaft has a first portion which tapers inwardly from the conically tapered male portion towards the distal tip.

The solid body has a groove with a diameter less than a minimum diameter of either the intermediate tapered male portion or the proximal tapered end portion.

The distal shaft of the solid body portion has a second portion distal of the first portion which tapers outwardly towards the distal tip.

Other aspects of the invention are provided by an implant for replacing the proximal portion of a femur having a substantially intact natural femoral neck and a lateral side opposite the femoral neck, with a bore extending from the femoral neck through a lateral side of the femur. The implant comprises a sleeve having a flange for engaging a proximally facing resected surface of the neck surrounding the bore in the femur and having a bore with an inwardly tapered conical portion. A one-piece shaft element having an intermediate conically tapered male portion for mating with the tapered portion of the sleeve bone is provided. The shaft having a proximal end including a conically tapered proximal end portion and a distal shaft portion having an enlarged unthreaded tip with a diameter less than a diameter of the bore from the femoral neck through the lateral side of the femur. A head member having a distal end and a proximal substantially-spherical portion is configured for positioning in a natural or prosthetic hip socket. The distal end of the head member including a conically tapered bore for coupling to the proximal conically tapered portion of the solid body member; and wherein no threaded elements pass within or through the femur.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

DETAILED DESCRIPTION

Figure 1:
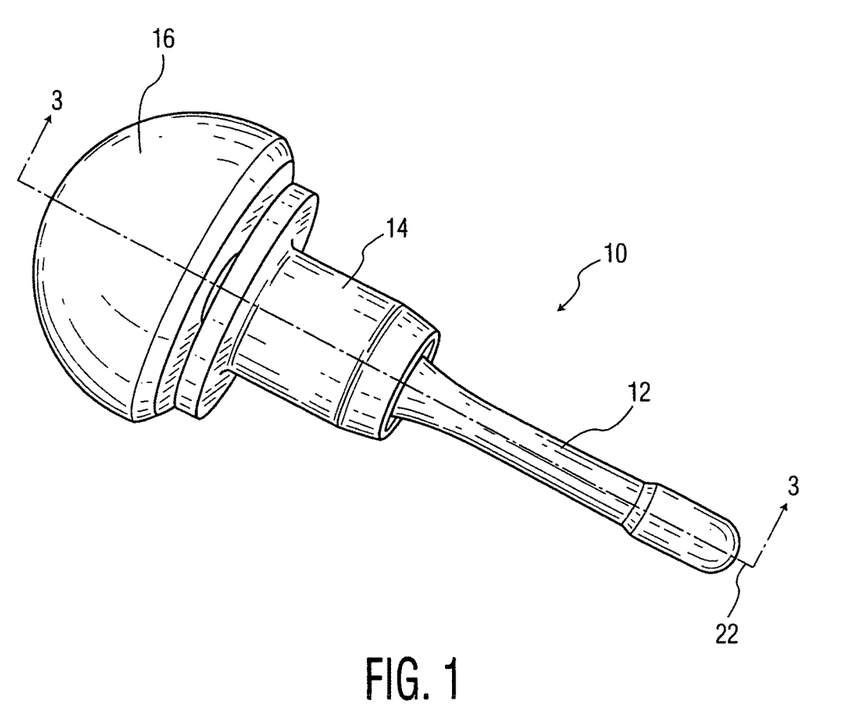
FIG. 1 is an isometric view of an assembled femoral head prosthesis of the present invention.

Referring to FIG. 1 there is shown a femoral head prosthesis generally denoted as 10 which comprises a shaft or intermediate solid body member 12, a sleeve 14 and a part spherical femoral prosthetic head 16. FIG. 1 shows the elements 12, 14 and 16 in an assembled configuration.

Figure 2:
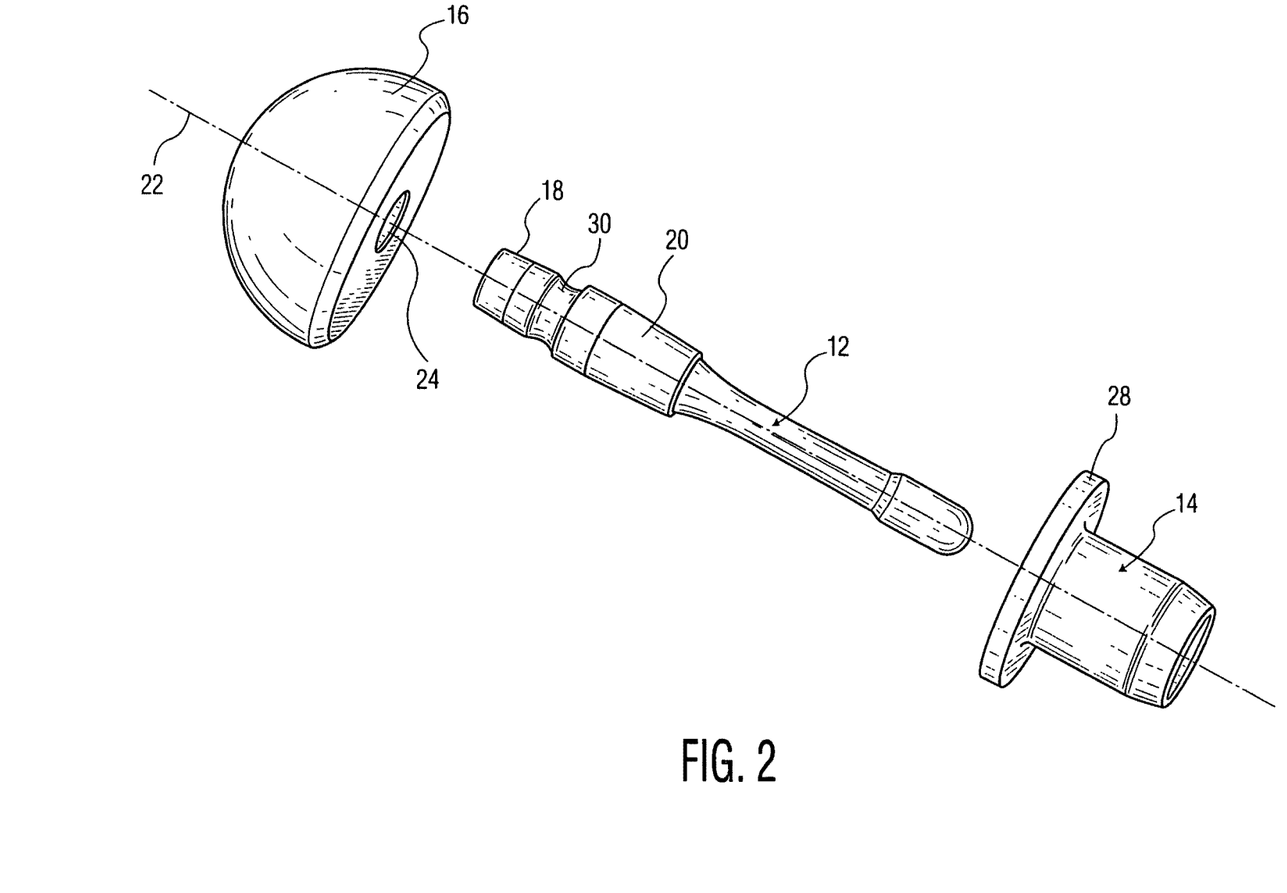
FIG. 2 is an exploded view of the femoral head prosthesis of FIG. 2.

Referring to FIG. 2 there is shown an exploded view of the femoral head prosthesis of FIG. 1 with the proximal prosthetic femoral head 16 separated proximally from shaft 12 and the sleeve 14 separated distally of the shaft 12. It can be seen that shaft or intermediate solid body member 12 includes a proximal conically tapered male portion 18 and an intermediate conically tapered male portion 20. In the preferred embodiment conically tapered portion 18 is tapered towards the longitudinal axis 22 of shaft 12 while moving from a distal to proximal direction. The intermediate tapered portion 20 is tapered towards longitudinal axis 22 on moving from the proximal to distal direction.

Figure 3:
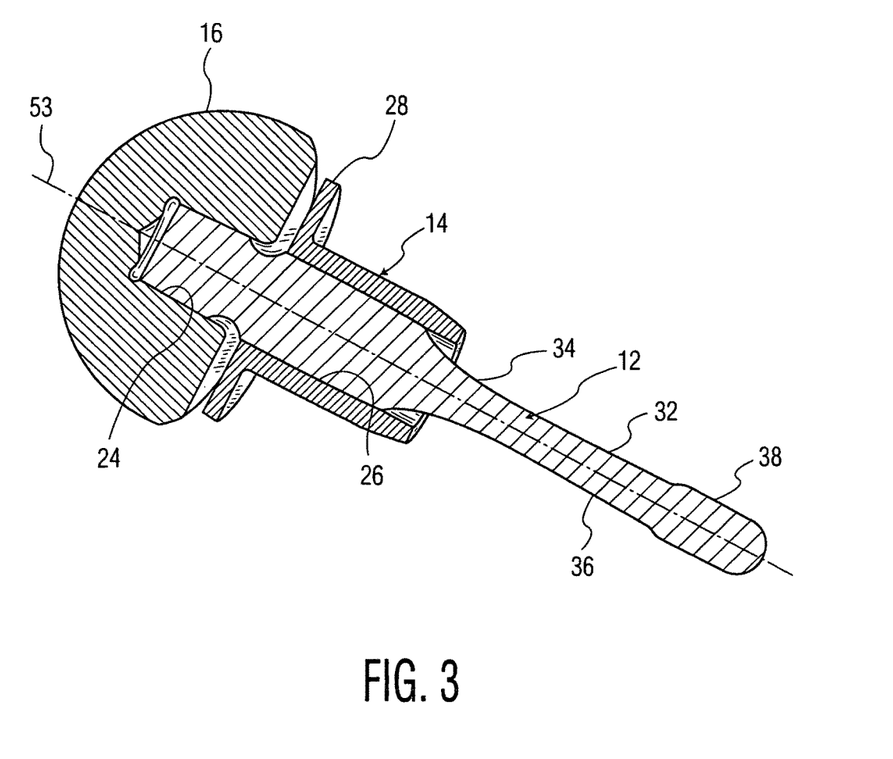
FIG. 3 is a cross-sectional view of the femoral head prosthesis of FIG. 1 along lines 3-3 thereof.

As best seen in FIG. 3 both head 16 and sleeve 14 have complimentary conically tapered female bores 24 and 26 respectively which form interlocking connections with portions 18 and 20 of shaft 12 respectively. In a preferred embodiment these tapers are the well known Morse tapers but any connection design may be used. Sleeve 14 includes a flange portion 28 which extends radially outwardly from the outer surface of sleeve 14 surrounding bore 26 and is open to receive shaft 12.

Figure 5:
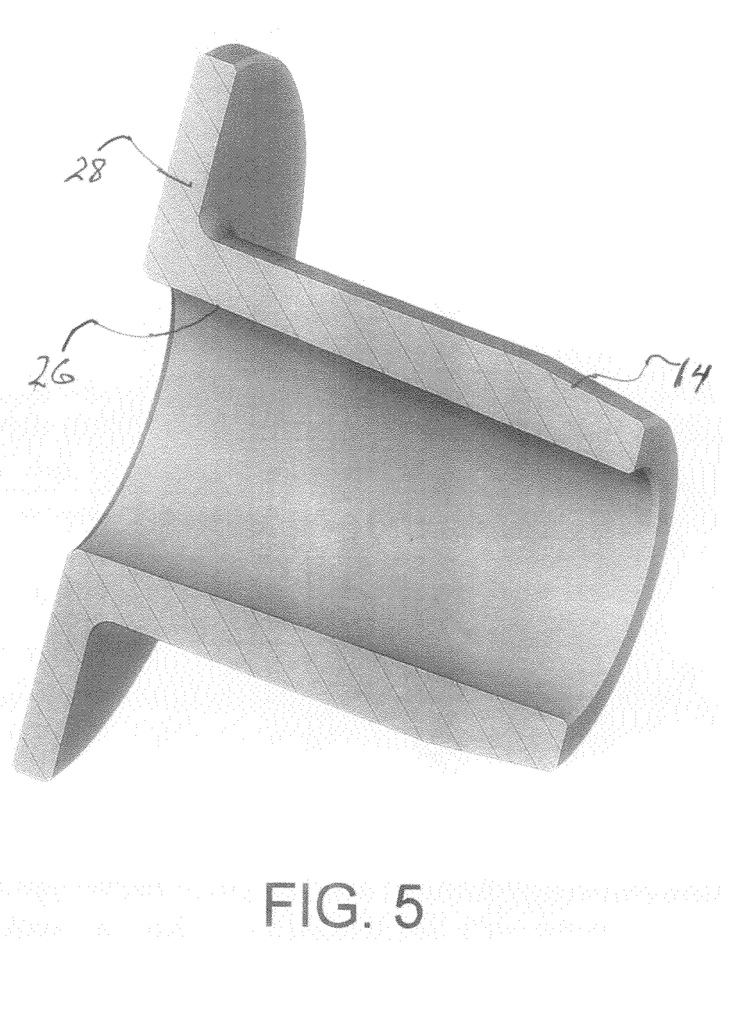
FIG. 5 is a cross-sectional view of the sleeve component of FIG. 1.
Figure 6:
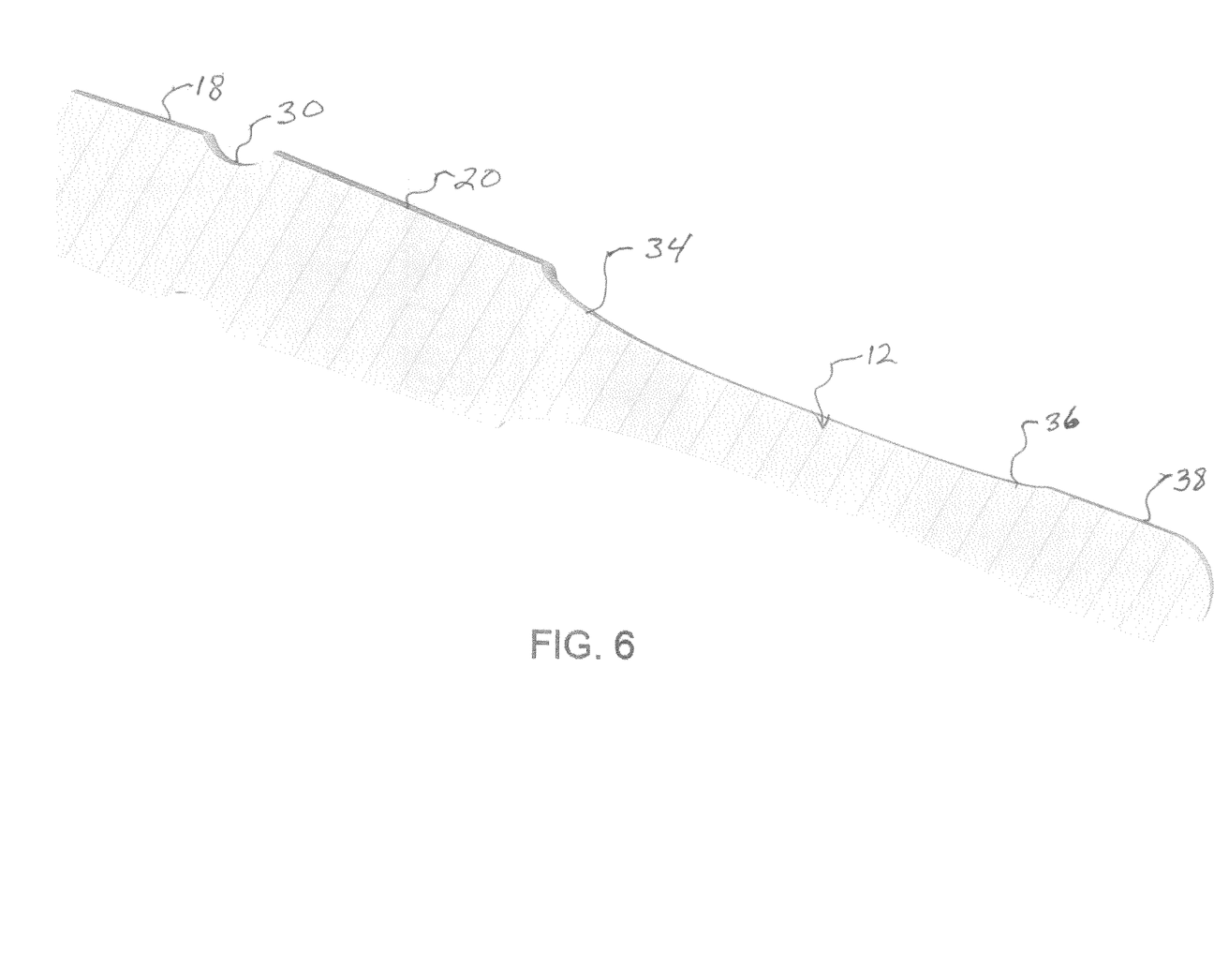
FIG. 6 is a cross-sectional view of the shaft component of FIG. 1.

Referring to FIGS. 2, 3 and 5, shaft 12 includes an annular groove 30 which separates tapered portions 18 and 20 thereof. The function of groove 30 is provided as a transition area between the femoral head taper and sleeve taper. Also shown is the distal shaft portion 32 of shaft 12 which has a first portion 34 which tapers inwardly towards the longitudinal axis 22 on moving along the distal shaft 32 in a proximal to distal direction. Shaft 12 has a second portion 36 which expands in diameter on moving from the proximal to distal direction which portion ends in an enlarged tip 38 which, in the preferred embodiment, has a generally cylindrical smooth outer surface. The smooth outer surface of tip 38 allows sliding contact between shaft 12 and the lateral cortex. The shaft 12 is contoured to provide as well as fatigue resistance (strength).

Figure 4:
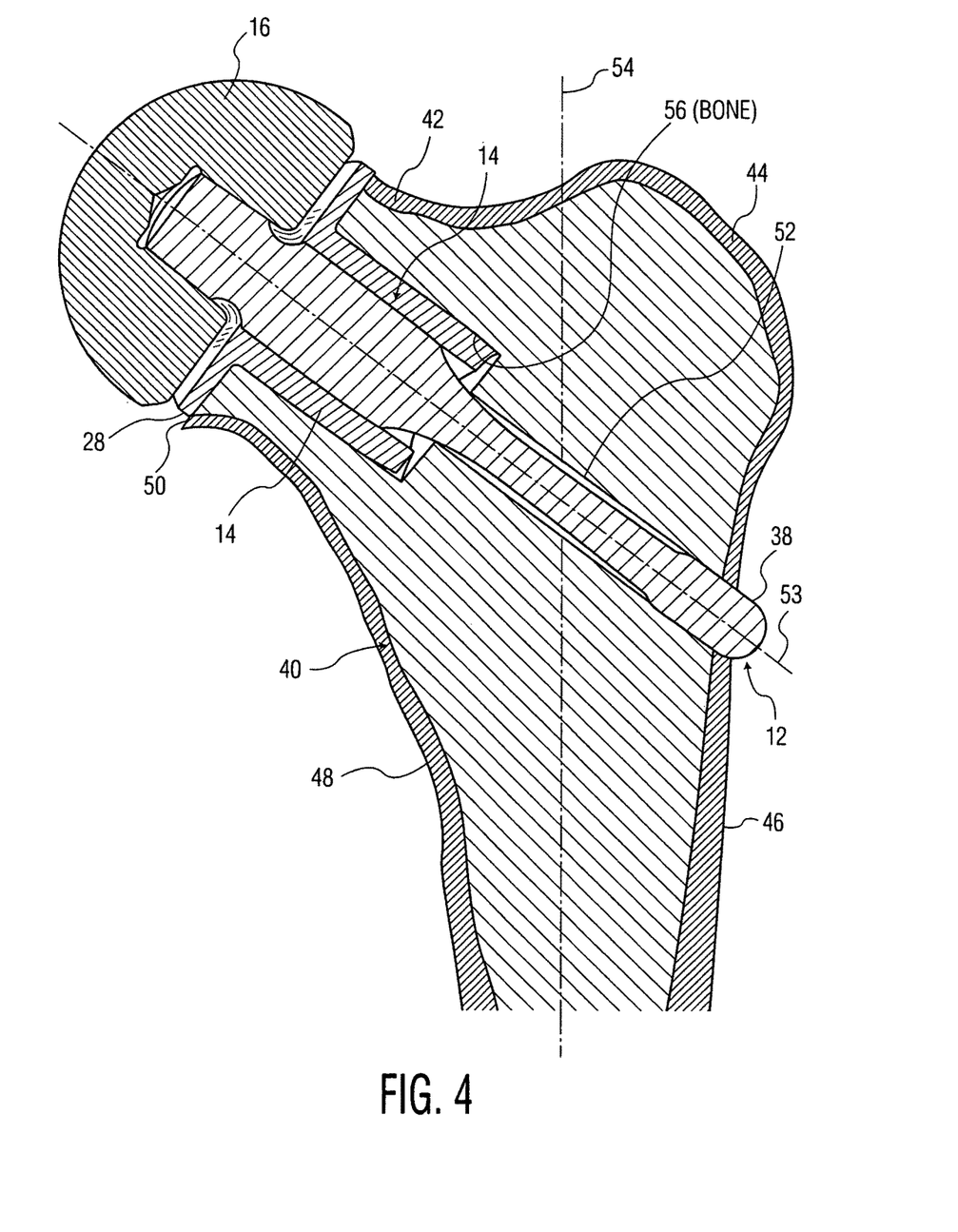
FIG. 4 is a cross-sectional view of the prosthesis of FIG. 1 implanted in a femur.

Referring to FIG. 4 there is shown the femoral head prosthesis implanted in a proximal femur 40. As shown in FIG. 4 femur 40 includes a neck portion 42, a trocanteric region 44, a lateral side 46 and a medial side 48. In the preferred surgical method the natural femoral head is resected and removed at a point on the neck 42 which is proximal to the narrowest area or isthmus on the natural neck of the femur. The flange 28 of sleeve 14 has a diameter which is greater than or, preferably, equal to the outer diameter of the proximal end face 50 of the bone of resected neck 42. As will be discussed below, the femoral head prosthesis of the present invention is supplied as a kit including different size heads, sleeves and shafts so that replacement of different size natural femurs can be accommodated. In the preferred embodiment all the interconnected portions have the same size taper regardless of implant size.

Prior to inserting the femoral head prosthesis 10 of the present invention into the femur 40 a first bore 52 is drilled in the femur from the resected neck 42 and through to the lateral side 46 of femur 40 in a medial to lateral direction at an angle to the proximal distal direction. In the preferred embodiment this angle is 135° with respect to the anatomic axis of the femur 54 which is the natural or neutral neck angle. This is the approximate neck angle of the femur. The bore in the neck has a diameter that is greater than or equal to tip 38 of shaft 12. This allows the tip 38 to extend beyond lateral surface 46 of femur 40 and subside slightly after implantation. Once bore 52 is made a counter bore 56 is made concentric about the axis 53 of first bore 52. The diameter of counter bore 56 is equal to or slightly greater than the outer diameter of sleeve 14. Initially sleeve 14 is implanted in the counter bore 56 and thereafter shaft 12 is inserted such that tip 38 extends beyond the lateral surface 46 of femur 40 and conically tapered male portion 20 of shaft 12 lockingly engages conically tapered female portion 26 of sleeve 14. Lastly head 16 is placed on the conically tapered proximal portion or trunion 18 and taper locked thereon in a standard manner.

As discussed above, the three elements 12, 14 and 16 may be supplied as a kit of such elements. For example, the prosthetic head 16 may have a spherical diameter of 28 or 32 mm with the shaft having a length of about 40-60 mm. In addition, a variety of sleeves 14 may be provided with flanges of different diameters for example, 23 mm. In the preferred kit there are two heads and four sleeves and three shafts. The provision of similar tapers allow independent component sizing due to modularity of the components. Thus they can be mixed for form different size implants.

Since there is no direct connection between shaft 12 and the femur, the load on head 16 is applied to femur 40 through sleeve 14 exclusively. As discussed above, this simulates the natural loading of the femur by forces acting through the femur neck. The distal end of 12 interacts with the femur thus the load of the head travels through the shaft or intermediate member and the intermediate member interacts with sleeve and lateral cortex.

The advantage of the proposed design is that it can be implanted through one relatively small incision. Since the implant is modular the heads 16 shafts 12 and sleeves 14 can be mixed to provide a number of different implants.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention is claimed is:

1. An implant for replacing the proximal portion of a femur having a substantially intact natural femoral neck and a lateral side opposite the femoral neck, with a bore extending through the femoral neck through a lateral side of the femur, the bore having an opening through cortical bone at the lateral side of the femur, the implant comprising:

a sleeve having a flange for engaging a proximally facing resected surface of the neck surrounding the bore in the femur and having an extension with an outer cylindrical surface matching an inner surface of the bore in the femur integrally formed with the flange, extension having a bore with a conical portion tapered inwardly on moving from proximal to distal;

a solid body member having a longitudinal axis, a distal end, and a proximal end, being configured for positioning, in use, in the bore through the femur, the distal end having a cylindrical distal tip with a smooth outer surface, the body member having a distal shaft portion of sufficient length to locate the cylindrical distal tip at least partially beyond the bore opening through the cortical bone at the lateral side of the femur, the solid body member having an intermediate conically tapered male portion tapered inwardly on moving in a proximal to distal direction for coupling to the conically tapered bore of the sleeve and a proximal end having a conically tapered portion which tapers inwardly on moving in a distal to proximal direction;

a head member having a distal end and a proximal substantially-spherical portion configured for positioning in a natural or prosthetic hip socket, the distal end of the head member including a conically tapered bore for coupling to the proximal conically tapered portion of the solid body member; and wherein no threaded elements pass within or through the femur.

2. The implant as set forth in claim 1 wherein the distal shaft portion has a first portion immediately distal of the intermediate conically tapered male portion which tapers inwardly from a proximal end towards the cylindrical distal tip.

3. The implant as set forth in claim 1 wherein the distal shaft portion of the solid body member has a first inwardly tapered section intermediate the cylindrical distal tip and the proximal end of the solid body member.

4. The implant as set forth in claim 3 wherein the cylindrical distal tip has a diameter generally equal to or less than the diameter of the bore in the femur.

5. The implant as set forth in claim 3 wherein the solid body member has a groove with a diameter less than a minimum diameter of either the intermediate conically tapered male portion or the proximal end tapered portion.

6. The implant as set forth in claim 5 wherein the distal shaft portion has a second portion distal of the first inwardly tapered section which tapers outwardly towards the cylindrical distal tip.

7. An implant for replacing the proximal portion of a femur having a substantially intact natural femoral neck and a lateral side opposite the femoral neck, with a bore extending through the femoral neck through a lateral side of the femur, the bore having an opening through the cortical bone at the lateral side of the femur, the implant comprising:

a sleeve having a flange for engaging a proximally facing resected surface of the neck surrounding the bore in the femur and having an extension with an outer cylindrical surface matching an inner surface of the bore in the femur integrally formed with the flange, the extension having a bore with an inwardly tapered conical portion;

a one-piece shaft element having an intermediate conically tapered male portion for mating with the tapered conical portion of the sleeve bore, the shaft element having a proximal end including a conically tapered proximal end portion and a distal shaft portion having an enlarged unthreaded tip with a smooth cylindrical outer surface, the distal shaft portion having a diameter less than a diameter of the bore from the femoral neck through the lateral side of the femur, the distal shaft portion having a length placing the tip cylindrical outer surface at least partially beyond the bore opening through cortical bone at the lateral side of the femur;

a head member having a distal end and a proximal substantially-spherical portion configured for positioning in a natural or prosthetic hip socket, the distal end of the head member including a conically tapered bore for coupling to the conically tapered proximal end portion of the shaft element; and wherein no threaded elements pass within or through the femur.

8. The implant as set forth in claim 7 wherein the distal shaft portion of the shaft element has an inwardly tapered section.

9. The implant as set forth in claim 8 wherein the distal shaft portion tip has a diameter generally equal to the diameter of the bore in the femur.

10. The implant as set forth in claim 7 wherein the distal shaft portion has a first portion immediately distal of the intermediate conically tapered male portion which tapers inwardly from a proximal end towards the tip.

11. The implant as set forth in claim 7 wherein the shaft element has a groove with a diameter less than a minimum diameter of both the intermediate conically tapered male portion and the conically tapered proximal end portion of the shaft element.

12. The implant as set forth in claim 11 wherein the distal shaft portion has a second portion distal of the conically tapered proximal end portion which second portion tapers outwardly towards the tip.

* * * * *